United States Patent [19]

Wisniewski et al.

[11] Patent Number: 4,806,627

[45] Date of Patent: Feb. 21, 1989

[54] HYBRID CELL LINES PRODUCING MONOCLONAL ANTIBODIES DIRCTED AGAINST SCRAPIE-ASSOCIATED FIBRIL PROTEINS

[75] Inventors: Henryk M. Wisniewski, Staten Island, N.Y.; Richard J. Kascsak, Middletown, N.J.; Richard Rubenstein, Staten Island, N.Y.; Patricia A. Merz, Staten Island, N.Y.; Maria Tonna-DeMasi, Staten Island, N.Y.

[73] Assignee: Research Foundation of Mental Hygiene Inc., Albany, N.Y.

[21] Appl. No.: 55,708

[22] Filed: May 29, 1987

[51] Int. Cl.[4] .................. A61K 39/395; C07K 15/14
[52] U.S. Cl. ............... 530/387; 435/240.27; 435/68; 435/7; 424/85.8; 935/103; 935/104
[58] Field of Search .......... 530/387; 424/85; 935/95; 435/172.2, 68, 240.27

[56] References Cited

U.S. PATENT DOCUMENTS 4,666,829  5/1987  Glenner et al. ............... 435/68

OTHER PUBLICATIONS

Merz et al., Science, 225: 437–9, (1984).
Bendheim et al., P.N.A.S., 82: 997–1001, Feb. 1985.
Bendheim et al., Nature, 310, Aug. 1984, pp. 418–421.
Brown et al., New Eng. J. Med., 314(a), 547–51, Feb. 27, 1986.
Bockman et al., N.E.J.M., 312(2), 73–78, (1985).
Cho, J. Gen Virology., 67, 243–53, 1986.
J. Gen Virol., 61(1), Jan. 1987, 42–9, Merz et al.
Rubenstein et al., 67, 671–81, 1986.
Kohler et al., Nature, 256, 495–497, 1975.

*Primary Examiner*—Howard E. Schain
*Assistant Examiner*—Jeff. P. Kushan
*Attorney, Agent, or Firm*—Morgan & Finnegan

[57] ABSTRACT

Hybridoma tumor cell line ATCC No. HB9222. A monoclonal antibody, specific for scrapie-associated fibrils and the proteins which comprise scrapie-associated fibrils, produced by said cell line.

2 Claims, No Drawings

HYBRID CELL LINES PRODUCING MONOCLONAL ANTIBODIES DIRCTED AGAINST SCRAPIE-ASSOCIATED FIBRIL PROTEINS

BACKGROUND OF THE INVENTION

The present invention relates to hybrid cell lines capable of continuously producing monoclonal antibodies specific for scrapie-associated fibrils (SAF). The proteins which comprise SAF, also known as PrP's (protease resistant proteins) are observed only in the unconventional slow virus diseases (UNSVD).

UNSVD are progressive degenerative diseases of the central nervous system which are lethal. These diseases naturally affect sheep, goats, mule deer, elk and humans and can be experimentally transmitted to primates and rodents. The human diseases include: Creutzfeldt-Jakob disease (CJD), kuru and Gerstmann Sträussler syndrome (GSS), a familiar disease occurring with an autosomal dominant mode of inheritance, while the animal disease in sheep and goats is known as scrapie and the disease of mule deer and elk known as chronic wasting disease. At present, the diagnosis of UNSVD is based on the clinical signs and neuropathology. Conclusive evidence for the diagnosis is the transmission of this disease to animals which may take as long as ten years. SAF are abnormal filamentous structures uniquely and specifically associated with UNSVD. Numerous studies employing tissue from many human neurological diseases and from many experimental and natural animal model systems have shown that SAF are found only in the UNSVD. The SAF are composed of a PrP which in addition to the fibrils is disease specific.

The scrapie-like infectious agents elicit no antibody response in the host, nor does immunosuppression with whole body radiation, cortisone, antileukocytic serum, or cytotoxic drugs alter the incubation period, progress or pattern of disease, or length of illness to death. The scrapie-like infectious agents replicate peripherally, notably in spleen and lymph nodes, but only cause pathology in the central nervous system. In addition, these disease agents do not replicate well in cell culture systems. These disease agents have enormous resistance to the normal physical and chemical virological inactivation systems. This is shown by their resistance to high concentration of formaldehyde or glutaraldehyde and most other antiviral and antiseptic substances and to ultraviolet and ionizing radiation, to ultrasonication and to heat. Numerous organic disinfectants, including detergents and the quaternary ammonium salts, often used for disinfection are inadequate for inactivating these disease agents. They are, however, susceptible to certain proteases and strong denaturing compounds such as phenol, chlorox, potassium permanganate and sodium hydroxide. Thus, much more stringent and harsh procedures must be used to ensure decontamination and disinfection.

The rapid and specific diagnosis of UNSVD will be of tremendous service to the medical community, since human CJD has been transmitted by surgical procedures, organ transplant, electrode implantations, and treatment with biological products such as human growth hormone and dura mater. Patients involved in surgical or transplantation procedures cannot be screened at the present time for the presence of scrapie-like infectious agents in that no test procedure is available. Analogous to blood products relative to AIDS, procedure should be available to screen human biological products for UNSVD agents. This diagnosis is crucial for hospital workers in view of the ever-increasing geriatric population and potential for transmission of the disease to others during surgical procedures. These agents are fatal when transmitted and diagnostic tests are needed which will help in distinguishing the CJD dementias from Alzheimer's disease. Such diagnostic tests, using monoclonal antibodies are provided by this invention.

A key breakthrough in the study of UNSVD was the discovery of an abnormal fibril, scrapie-associated fibrils (SAF), present exculsively in extracts of brains exclusively in these diseases (Merz et al. Acta Neuropathol. 54:63–74, 1981; Merz et al. Nature 306:474–476, 1983; Merz et al. Science 225:437–440, 1984). SAF have been shown to be unique to naturally occurring or experimentally induced UNSVD (Merz et al. Science 225:437–440, 1984). SAF are composed of a modified protease resistant form of a host sialoglycoprotein, PrP (Bolton et al. Science 218:1309–1311, 1982; Merz et al. J. of Virol. 61:42–49, 1987). In experiments designed to isolate infectivity, co-purification of SAF, PrP and infectivity was achieved (Diringer et al. Euro. J. Biochem. 134:555–560, 1983; Prusiner et al. Cell 35:349–358, 1983).

PrP are glycosylated cleavage products of a larger host glycoprotein of 33–35 Kda (Oesch et al. Cell 40:735–746, 1985; Manuelidis et al. Proc. Nat. Acad. Sci. 82:4263–4267, 1985; Rubenstein et al. J. Gen. Virol. 67:671–681, 1986). The detection of this protein in a fibrillar form (SAF) or a non-fibrillar form is diagnostic for UNSVD, (Merz et al. Science 225:437–440, 1984; Brown et al. N. Eng. J. of Med. 314:547–551, 1986). Several isolation procedures have been developed to isolate both SAF and PrP (McKinley et al. Cell 35:57—62, 1983, Helmert and Diringer, Bioscience. Rep. 4:165–170, 1984; Hope et al. EMBO J. 5:2591–2597, 1986). The ability to obtain large quantities of purified PrP and SAF has allowed for the production of polyclonal antibodies to PrP (Bendheim et al. Nature 310:418–421, 1984; Diringer et al. Lancet ii 345, 1984; Kascsak et al. J. of Virol. 59:676–683, 1986; Takahashi et al. Microbiol. Immunol. 30:123–131, 1986). Monoclonal antibodies have been produced to hamster PrP which react exclusively with hamster protein (Barry et al. J. Infect. Dis 154:578–521). These antibodies have been used to specifically identify both SAF and PrP by various immunological means. The western blot procedure has frequently been used to identify PrP in human and animal UNSVD (Bendheim et al. Proc. Nat. Acad. Sci. 82:997–1001, 1985; Bockman et al. N. Eng. J. Med. 312:73–78, 1985; Kascsak et al. J. of Virol. 59:676–683, 1986; Brown et al. N. eng. J. Med. 314:547–551, 1986; Gibbs et al. N. Eng. J. Med. 313:734–738, 1985). SAF have also been identified by immunodecoration (Barry et al. J. of Immun. 135:603–613, 1985; Merz et al. J. of Virol. 61:42–49, 1987). The amyloid present in certain UNSVD also appears to be composed of PrP which differentiates this type of amyloid from amyloids found in other neurological diseases. Antibody to PrP has been used to specifically stain amyloid using immunocytochemistry in UNSVD (DeArmond et al. Cell 41:221–235, 1985; Merz et al. Discussions in Neurosciences 3:458–468, 1986; Roberts et al. N. Eng. J. Med. 315:1231–1232, 1986).

SUMMARY OF THE INVENTION

The present invention provides a novel hybridoma cell line, ATCC HB 9222, which provides as a component of the supernatant of its growth the highly specific monoclonal antibody, 263K 3F4. Cell line ATCC HB 9222 was deposited in the American Type Culture Collection, 12301 Parklawn Drive, Rockville, Md. 20852, a recognized public depository for strains of microorganisms on Oct. 8, 1986. The present invention provides a cell line to produce a novel monoclonal antibody to specifically react with scraPie-associated fibril proteins. The hybridoma comprises a fused cell hybrid of a mouse spleen cell fused to a mouse myeloma.

The hybridoma cell line of the present invention was prepared by first immunizing mice by injection of scrapie-associated fibril proteins. Spleen cells were removed and fused with mouse myeloma cells in the presence of a fusion promoter. The fused cells were diluted and cultured in separate wells in a medium which will not support the unfused myeloma or spleen cells. The supernatant in each well was evaluated for the presence of antibody to scrapie-associated fibril protein. A hybridoma producing an antibody reacting with scrapie-associated fibril protein was selected and cloned. The antibody was recovered from a supernatant of the clone. The antibody reacted with the immunizing scrapie-associated fibril protein. A diagnostic method for detecting the presence of unconventional slow viral disease comprised contacting a specimen such as brain biopsy or autopsy tissue, lymph node biopsy or autopsy tissue, spleen biopsy or autopsy tissue, cerebrospinal fluid or buffy coat cells with the monoclonal antibody of the present invention that is capable of specifically binding to scrapie-associated fibril protein in an antigen-antibody complex and detecting the material bound by the antibody by immunological means such as enzyme-linked immunoabsorbent assay, Western blot assay, dot blot assay, immunodecoration and immunocytochemistry. It is one object of this invention to provide a hybridoma which produces a monoclonal antibody against a scrapie-associated fibril protein associated with unconventional slow viral disease. Another object of this invention is to provide methods for detection of scrapie-associated fibril protein. Other objects and advantages of the invention will become apparent from the examination of the present disclosure.

DETAILED DESCRIPTION OF THE INVENTION

The following examples illustrate a particular embodiment of the invention but they are not intended to limit it.

EXAMPLE 1

Preparation Of The Immunogen

Hamsters of the LVG strain (Charles River Breeding Laboratories, Wilmington, Mass., USA) were infected with 263K PrP (Kimberlin & Walker, *J. Gen. Vir.* 34:295–304 (1977)). They were routinely inoculated intracerebrally with a 1% homogenate of brain from previously infected animals (0.04 ml). Mock-infected animals were inoculated with a 1% homogenate of brain from normal animals. Animals were killed after exhibiting clinical signs for three consecutive weeks and the brains were stored at $-70°$ C.

SAF were isolated from brains of infected animals by a modification of the procedure of Hilmert & Diringer, *Bioscience ReP.* 4:165–170 (1984). A 10% homogenate of infected brain (usually 12 g) was prepared in 10% sarcosyl using a Tekmar model TR-10 Tissumizer (two 30-s homogenizations). After incubation for 30 minutes at room temperature, homogenates were clarified by centrifugation at $22,000 \times g$ for 30 minutes at $20°$ C. The pellets were re-extracted and clarified as described above. Combined supernatants were centrifuged at $200,000 \times g$ for 2.5 hours at $20°$ C. The pellet was suspended by sonication (Branson model 185 sonifier with microtip at 25 W) in TBS (10 mM Trishydrochloride, 133 mM [NaCl pH 7.4]) containing 10% NaCl and 1% sarcosyl (TBSNS) and incubated overnight at room temperature. The suspension was pelleted at $200,000 \times g$ for 3.5 hours at $20°$ C. The pellet was suspended as before in TBSNS and shaken at $37°$ C. for 2 hours. The suspension was pelleted in a Microfuge (Beckman Instruments, Inc., Fullerton, Calif.) for 15 minutes at room temperature. The pellet was resuspended in TBSNS containing 50 μg of proteinase K (Merck Co., Inc., Rahway, N.J.) per ml and shaken at $37°$ C. for 2 hours. The suspension was pelleted in the Microfuge for 15 minutes and resuspended in $H_2O$ containing 0.1% sarcosyl and 1 mM phenylmethylsulphonylfluoride. The suspension was diluted to 8 ml, layered over a cushion of 20% sucrose, and centrifuged at $210,000 \times g$ for 5 hours at $20°$ C. The final pellet was suspended in 100 μl of TBS containing 0.1% sulphobetaine 3-14 (Calbiochem-Behring, La Jolla, Calif.). This final pellet contained 100 to 500 μg of PrP and 1 to 10% of infectivity found in the original homogenate.

EXAMPLE 2

Immunization of Animals

Balb c/J mice were immunized with 263K PrP solubilized in 77% formic acid. Six immunizations were Performed in the presence of adjuvant employing 20–30 ug PrP Per dose. Antigen was given subcutaneously and into the peritoneal cavity. Immune response to this protein was monitored by enzyme-linked immunoabsorbent assay (ELISA).

EXAMPLE 3

Hybridoma Production

One of the mice immunized with hamster 263K PrP was used to produce hybridomas. The mouse received a final immunization of antigen (30 μg) in PBS i.v. 4 days prior to fusion. Spleen cells were fused to myeloma cell line X63-Ag8.653 as previously described in Nowinski et al., Virology 93, 111–126 (1979) and Wang et al., Acta Neuropath 62, 268–275 (1984). Initial screening of hybridoma supernatants from 96 well plates was performed using the ELISA assay. One of the hybridomas (263K 3F4) was cloned three times by limiting dilution and used to produce ascites in pristane (Sigma, St. Louis, Mo.) primed mice, see Potter et al., J. Natl. Cancer Inst. 49, 305–308 (1972).

Over 400 wells containing hybridomas were screened and only three wells yielded ELISA readings indicative of a positive response to PrP. A positive response was defined as an optical density reading of $>1.0$ and a PrP/BSA antigen index ratio of $>10$, see Wang et al., Acta Neuropath 62, 268–275 (1984). Only one of these clones has been characterized. This clone designated 263K 3F4 produces immunoglobulin class IgG2A, Kappa chain. The immunoglobulin subtype of this clone was determined using mouse immunoglobulin subtype identification kit (Boehringer Mannheim Biochemicals, Indianapolis, Ind.) Ascites has been produced which has a titer of greater than $10^6$ by ELISA assay and $10^5$ by western blot assay.

EXAMPLE 4

Screening Hybridomas For Specific Antibodies

A. ELISA Assay

Formic acid extracted hamster PrP antigen was bound to ELISA trays (Falcon-Micro test III) at 1 μg/ml in PBS at 37° C. for one hour and 4° C. overnight. Plates were blocked in PBS containing 2% normal goat serum and 0.2% tween 20 for 30 minutes at room temperature. Monoclonal antibody was reacted in this plate for two hours at 37° C. The plate was washed in PBS containing 0.2% tween 20 and secondary antibody (goat anti-mouse immunoglobulin conjugated with alkaline phosphatase) was added. This enzyme catalyzed conversion of the substrate, p-nitrophenyl phosphate to p-nitrophenol, caused a chromogenic change observed by a rise in the optical density of the solution at 405 nm. This rise in optical density was read spectrophotometrically and directly related to the amount of monoclonal antibody binding to PrP antigen. The results of ELISA assays using 3F4 is set out in Table I. ELISA assays have also shown that this antibody is not reactive to microtubules, neurofilaments or paired helical filaments.

TABLE 1
ELISA Assay

| Antibody source | dilution | antigen* 263K PrP | BSA |
|---|---|---|---|
| normal mouse plasma | $1.10^3$ | 13** | 20 |
| polyclonal mouse anti 263K PrP | $1.10^4$ | >1500 | 16 |
|  | $1.10^5$ | 250 | 10 |
| 263K 3F4 First cloning | undiluted | >1500 | 18 |
| 263K 3F4 Second cloning | undiluted | >1500 | 24 |
| 263K 3F4 Third cloning | undiluted | >1500 | 16 |
| 263K 3F4 ascites | $1.10^4$ | >1500 | 10 |
|  | $1.10^5$ | >1500 | 26 |
|  | $1.10^6$ | 390 | 10 |

*antigens bound in PBS at 1 ug/ml
**average of duplicate optical density readings at 405 nm

B. Western Blots

Samples containing PrP from various species were electrophoresed on 15% polyacrylamide gels and electrophoretically transferred to nitrocellulose paper (NC) (Kascsak et al. *J. Virol.* 1986 in press, Rubenstein et al., *J. Gen. Virol.*, 1986). Unbound sites on NC were blocked using PBS containing 2% BSA and 2% normal goat serum for 30 minutes at room temperature. Primary antibody (263K 3F4 ascites at 1:50,000 in PBS containing 1% normal goat serum and 0.2% tween 20) was added to the NC blot for two hours at 37° C. on a rocker platform. Blot was washed with PBS containing 0.2% tween 20 and secondary antibody (goat anti-mouse conjugated with alkaline phosphatase) added. The blot was then incubated for 1.5 hours at 37° C. on the rocker platform. The blot was then washed as before and substrate added. The substrate consisted of nitroblue tetrazolium (0.33 mg/ml) and 4-bromo-4-chloro-3-indolyl phosphate (0.17 mg/ml) in 0.1M Tris, 0.1M NaCl, 0.05M $MgCl_2$ pH 9.5. A blue precipitate formed on the blot where the antigen had reacted with the antibody. Reaction was stopped by washing the blot in water.

The 263K 3F4 ascites reacted with hamster PrP and not PrP isolated from mice infected with various scrapie agents. The 263K 3F4 antibody also reacted with the normal 33–35 Kda protein in brain homogenates from hamsters and humans. The antibody did not react with normal brain proteins from mice, rats or sheep. These results emphasize the specificity of 263K 3F4 for PrP and 33–35 Kda protein.

C. Immunodecoration

Purified SAF isolated from C57BL/6J mice infected with ME7, 139A, and 22L scrapie agents and from LVG hamsters infected with 263K agent were examined by immune electron microscopy for reaction with 263K 3F4 monoclonal antibody. A 5 μl sample of SAF was placed on a freshly glow discharged carbon coated 400 mesh nickel grid for one minute, drained and washed with two drops of fresh glass distilled water. The specimen was placed in a drop of 0.1% BSA in 0.04M PBS or 0.04M TBS pH 7.2 for ten minutes, drained and placed on a drop of antibody (diluted in PBS or TBS) for one hour. The specimen was drained again, washed and incubated on a drop of goat anti-mouse immunoglobulin conjugated with colloidal gold for one hour. The specimen was then washed in TBS or PBS and stained with 2% uranyl acetate for 45 seconds. The sample was washed with a drop of water, air dried and then examined in an electron microscope. A positive reaction was indicated by deposition of gold particles on SAF. The 263K 3F4 monoclonal antibody reacted by immunodecoration with 263K hamster SAF but not mouse SAF isolated from animals infected with ME7,139A or 22L scrapie agents. This Procedure has also been used on the airfuge prepared samples for diagnosis of human unconventional slow viral diseases.

Immunocytochemistry was also used to characterize 263K 3F4 monoclonal antibody. Formalin fixed tissue sections were prepared from the brains of mice and hamsters infected with scrapie. Amyloid plaques were detected in these sections by thioflavin S staining. Unstained sections were reacted with 263K 3F4 and the reaction was monitored using a peroxidasediaminobenzidine assay system. No reaction was seen with the amyloid plaques in hamster or mouse brain tissue sections at the level of light microscopic observation.

EXAMPLE 5

Diagnosis of Human Unconventional Slow Viral Disease Using Patient Brain Biopsy Tissue A 20% tissue homogenate was prepared in 10% sarcosyl. The homogenate was clarified at 1000 xg for five minutes. Supernatant was centrifuged in an airfuge at 130,000×g for two hours. The pellet was resuspended in tris buffered saline containing 0.1% sulfobetain SB-14 and centrifuged at 130,000 ×g for one hour. As little as 20–40 mg was needed to prepare this sample. A sample equivalent to 50 μl of the original starting material was electrophoresed on a 15% polyacrylamide gel and electrophoretically transferred to nitrocellulose paper. Using the Western blot procedure, samples were analyzed for reactivity with 263K 3F4 monoclonal antibody. Blots were developed employing secondary antibody produced in goats to mouse immunoglobulin conjugated with alkaline phosphatase as described in Example 4. Results have shown the detection of PrP in seven of seven CJD cases and in none of seven non-CJD cases. There are no false possible results using this procedure since the normal protein of 33-35 Kda which reacts with 263K 3F4 was not isolated under these conditions. Also a dot blot procedure can be used for this analysis. The use of the dot blot procedure eliminates the need to perform electrophoresis and allows rapid analysis of a large number of samples. These fractions are also examined ultrastructurally for the presence of SAF by negative stain electron microscopy. The presence of these fibrils has been shown to be diagnostic for unconventional slow viral diseases (P. Merz et al., Science 225: 437–440 (1984)).

EXAMPLE 6

Diagnosis of Human Unconventional Slow Viral Disease Using Patient Brain Biopsy Tissue This brain tissue had been processed through an SAF purification protocol involving detergent and proteolytic enzyme treatment and differential centrifugation. Samples were examined by western blot (WB) analysis using 263K 3F4 ascites at a dilution of 1:50,000.

|  | Samples | SAF protein (WB) |
| --- | --- | --- |
| CJD | 2 | 2 |
| Kuru | 1 | 0 |
| GSS | 4 | 4 |
| Alzheimer | 3 | 0 |
| non-CJD | 2 | 0 |

All CJD and GSS samples were positive (6/6) using this assay system. The one Kuru case was negative. All control samples (patients not included in the unconventional slow virus disease category) were negative (0/5). A difference in WB profile was detected between CJD and GSS samples prepared and assayed in this manner.

A diagnostic test requires the use of small amounts of biopsy brain tissue. A procedure was developed which would require only milligrams of tissue. A 20% brain homogenate was prepared in 10% sarcosyl. The homogenate was centrifuged at 130,000×g for 1 hr. A sample equivalent to 50 μl of the original homogenate (10 mg of tissue) was examined by WB analysis using 263K 3F4 monoclonal antibody. An additional sample was examined by negative stain electron microscopy.

|  | Samples | SAF (negative stain) | SAF protein (WB) |
| --- | --- | --- | --- |
| CJD | 6 | 6 | 6 |
| non-CJD | 6 | 0 | 0 |

In this assay system, all CJD cases were positive (6/6), all non-CJD cases were negative (0/6). The airfuge procedure was particularly useful in that only small amounts of tissue were needed, the sample was prepared in 3 hrs. and treatment with proteolytic enzymes was not required.

The examination of brain tissue for SAF protein using monoclonal antibody 263K 3F4 was highly sensitive and specific. No false positives were detected (0/11). All cases of unconventional slow virus disease were diagnosed except the one case of Kuru. All CJD (8/8) and all GSS (4/4) cases were detected.

What is claimed:

1. A monoclonal antibody, 263K 3F4, produced by hybridoma cell line, ATCC HB 9222, and capable of specific binding to scrapie-associated fibril proteins in an antigen-antibody complex.

2. A hybridoma cell line, ATCC HB 9222, that produces a monoclonal antibody capable of specific binding to scrapie-associated fibril proteins in an antigen antibody complex.

* * * * *